United States Patent [19]

Milhaud

[11] 4,378,796
[45] Apr. 5, 1983

[54] ENDO-TRACHEAL OR TRACHEOTOMIC TUBE WITH SHIELD FOR ANAESTHESIA

[75] Inventor: Alain Milhaud, Amiens, France

[73] Assignee: PORGES Societe Anonyme, Paris, France

[21] Appl. No.: 339,488

[22] Filed: Jan. 15, 1982

[30] Foreign Application Priority Data

Apr. 17, 1981 [FR] France .............................. 81 07820

[51] Int. Cl.$^3$ .......................................... A61M 25/00
[52] U.S. Cl. .................................. 128/207.15; 604/98
[58] Field of Search ..................... 128/202.29, 203.12, 128/203.13, 203.15, 203.23, 203.24, 203.29, 204.18, 207.14, 207.15, 206.29, 303.1, 349 B; 138/DIG. 3, 145, 153, 172

[56] References Cited

U.S. PATENT DOCUMENTS

| Re. 30,365 | 8/1980 | Mattler | 128/349 B |
|---|---|---|---|
| 2,783,173 | 7/1954 | Walker et al. | 138/DIG. 3 |
| 3,322,126 | 5/1967 | Rüch et al. | 128/349 B |
| 3,529,633 | 8/1970 | Vaillancourt | 128/349 R |
| 3,683,908 | 8/1972 | Michael et al. | 128/207.15 |
| 3,854,484 | 12/1974 | Jackson | 128/207.15 |
| 4,090,518 | 5/1978 | Elam | 128/207.15 |
| 4,166,467 | 9/1979 | Abramson | 128/207.14 |

FOREIGN PATENT DOCUMENTS

| 609038 | 2/1935 | Fed. Rep. of Germany | 128/188 |
|---|---|---|---|
| 867144 | 2/1953 | Fed. Rep. of Germany | 128/349 B |

Primary Examiner—Henry J. Recla
Attorney, Agent, or Firm—Merriam, Marshall & Bicknell

[57] ABSTRACT

The present invention relates to an endo-tracheal or tracheotomic tube for anaesthesia, comprising a tubular body for conveying the ventilation and anaesthesia gases and provided in the vicinity of its distal end with an inflatable balloon ensuring tightness, a flexible thermal shield being disposed between said balloon and the proximal end of the tube, at some distance from said balloon. According to the invention, this tube comprises an auxiliary conduit opening on the side of said shield opposite the balloon adapted to have an inert gas passing therethrough. The invention is particularly applicable to the treatment of the upper respiratory tracts by laser.

2 Claims, 3 Drawing Figures

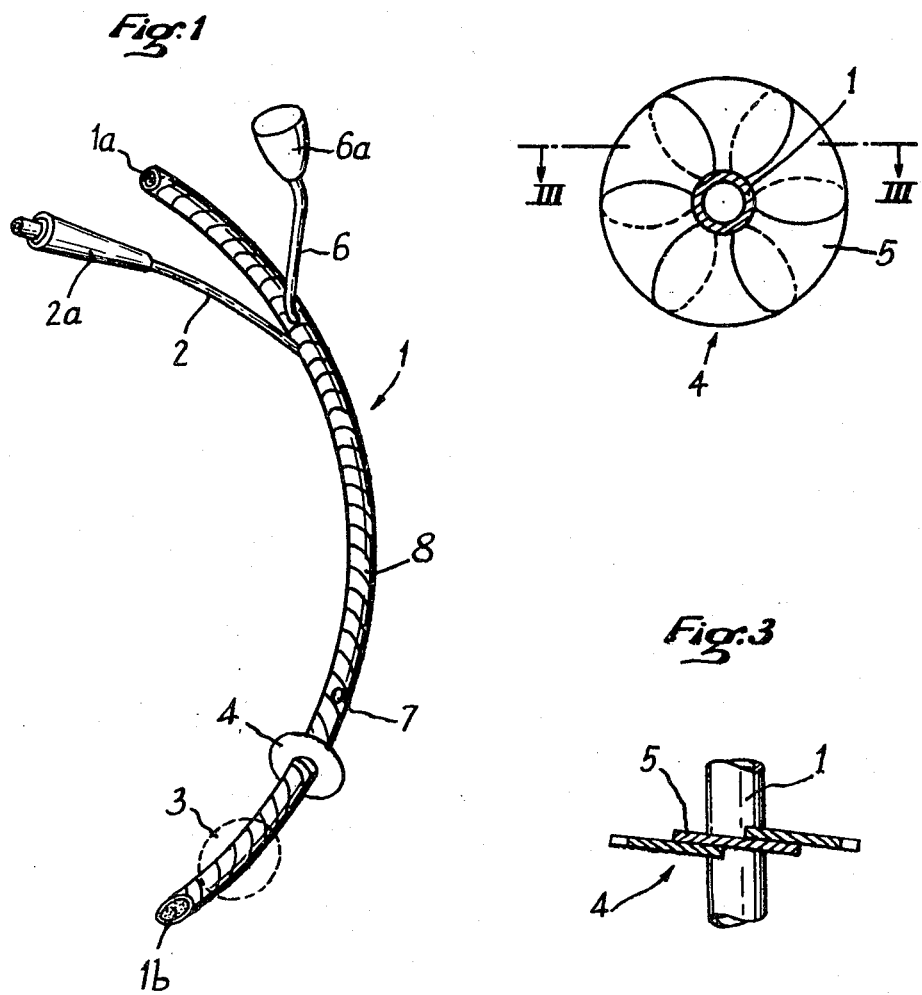

ENDO-TRACHEAL OR TRACHEOTOMIC TUBE WITH SHIELD FOR ANAESTHESIA

The present invention relates to an endo-tracheal tube or a tracheotomic tube with shield for anaesthesia, particularly for the treatment of pathological tissues of the upper respiratory tracts by laser.

An endo-tracheal tube for anaesthesia is already known, comprising a tubular body serving to convey the ventilation and anaesthesia gas and provided in the vicinity of its distal end with a balloon capable of being inflated from the outside, via an auxiliary conduit, so as to ensure tightness with the trachea and thus allow efficient ventilation. Such a tube, as well as its inflatable balloon, is constituted by natural or synthetic, organic matter, in order to be sufficiently flexible not to traumatize the respiratory tracts in which it is introduced.

This known endo-tracheal tube is entirely satisfactory in the case of a conventional operation, but, in the case of treatment by laser, which presents certain advantages over conventional operating techniques, difficulties appear.

In fact, the material constituting such a known endo-tracheal tube generally absorbs the infrared energy, with the result that, if an anaesthetic is delivered through this tube during an operation employing a laser, there is a risk of deterioration and even destruction of the tube for delivering the gases ensuring the patient's breathing. This may result in serious consequences for the patient, all the more so as the organic materials used for manufacturing the endo-tracheal tubes are not only combustible, but may also give off caustic or toxic vapours.

It may be that anaesthesia cannot be practised via the natural tracts or that, if the patient has already been treacheotomized, it is not an endo-tracheal tube which is used, but a tracheotomy tube provided with an anaesthesia balloon, or that, if the patient has already been tracheotomized, the cannula with which he is equipped is replaced by a flexible cannula provided with a balloon for anaesthesia.

The drawbacks of using the laser beam when the anaesthetic is delivered by tracheotomic tube and not by endo-tracheal tube, are, of course, the same.

In an attempt to remedy these drawbacks, it has already been thought to protect the endo-tracheal tube or the tracheotomic tube with helical winding of a strip made of a material reflecting the infrared energy, such as aluminum, these windings being for example fixed on the tube by means of an adhesive. Such a solution may be considered acceptable for protecting the tube itself, but it is without effect for protecting the balloon equipping the tube whose function is to ensure tightness and thus efficient ventilation. Now, it is precisely the balloon which is the most vulnerable part of the tube, as it is constituted by a very small thickness of an elastomer under tension.

It has also been thought to make the endo-tracheal tubes of a metallic material. However, in this case, rigid tubes are obtained which traumatize the respiratory tracts when inserted therein. Moreover, due to the specular polish of such an instrument, there is a risk of the laser beam reflecting on healthy tissues which do not have to be treated.

In order to remedy these drawbacks, Applicant has already described in French patent application No. 79 21218 of Aug. 23, 1979, an endo-tracheal or tracheotomic tube for anaesthesia comprising a tubular body serving to convey the ventilation and anaesthesia gases and provided in the vicinity of its distal end with an inflatable balloon providing tightness noteworthy in that it comprises between said balloon and the proximal end of the tube, at some distance from said balloon, a flexible thermal shield.

Thus, due to this flexible thermal shield, it is possible to obtain a flexible tube in which the balloon, which is the most fragile part, is protected by the thermal shield.

Such a thermal shield may be in the form of a disc coaxial to the tube. It may be fixed thereon or be integral therewith. It may be in one piece or, on the contrary, be constituted by a plurality of sectors fast with one another by slots with overlapping edges.

The thermal shield is preferably constituted by a flexible material similar to that of the tube and containing a dispersion of a finely divided metallic powder such as a powder of aluminum, silver, gold, etc . . . These metallic particles absorb and reflect the energy received from the impact of the laser beam treating pathological tissues.

Only the thermal shield may contain the dispersion of finely divided metal powder. However, it is advantageous if the whole of the tube comprises such a metallic dispersion, so that its resistance to the infrared energy is improved.

In the case of an endo-tracheal tube, the distance between the balloon and the shield is selected to be approximately equal to 2 or 3 cm so as to allow the vocal cords to be passed in two stages. In the case of a tracheotomic tube, the problem of passage of the vocal cords is obviously not raised. Under these circumstances, it is possible to place the thermal protection shield a few millimeters from the balloon ensuring tightness between the trachea and the tube. The diameter of the shield is selected, in both cases, to be slightly less that the diameter of the trachea to be intubated.

Furthermore, it is known that, during the treatment of the pathological tissues of the upper respiratory tracts, the patient is generally ventilated with an oxygen-rich mixture. An untimely bursting of the balloon eliminating tightness, or any other cause of leakage, would then allow the gaseous mixture contained in the lungs to flow back towards the upper part of the trachea and come into contact with the laser beam, which could cause untimely combustion of the endo-tracheal tube and of the mucous membranes treated by the laser.

Thus, despite the protective shield described hereinabove, adapted to maintain during the whole operation, the integrity of the tracheal balloon ensuring ventilatory tightness and preventing the reflux of the oxygen, there is still a danger that, either by lack of tightness of the balloon or due to its bursting, the upper part of the trachea can contain a gaseous mixture which is abnormally enriched with oxygen.

Moreover, it must be considered that air containing 20% of oxygen already constitutes an active combustion supporter. It is therefore necessary that the laser beams be made in an oxygen-poor atmosphere.

It is an object of the present invention to provide an endo-tracheal or tracheotomic tube for anaesthesia which avoids the above-mentioned drawbacks due to a lack of tightness or a bursting of the balloon.

To this end, according to the invention, the endo-tracheal or tracheotomic tube for anaesthesia comprising a tubular body serving to convey the ventilation and anaesthesia gases and provided, in the vicinity of its distal end, with an inflatable balloon providing tightness, a flexible thermal shield being disposed between said balloon and the proximal end of the tube, at some distance from said balloon, is noteworthy in that it comprises an auxiliary conduit opening on the side of said shield opposite the balloon and adapted to have an inert gas passing therethrough.

Thus, due to an auxiliary conduit, the upper part of the trachea (constituting to some extent the field of operation) can be permanently swept by a stream of nitrogen, for example. The inert gas thus fills all the upper part of the trachea.

Under these conditions, the risks of combustion are virtually eliminated.

Furthermore, it is known that the laser instrument is cumbersome and that the nasal intubation generally obliges the endo-tracheal tube to be placed in such positions that untimely blockage of the ventilation conduit of the tube may occur.

The tube according to the invention preferably comprises a helical reinforcement made of metal or a synthetic polyamide polyester yarn for example, preventing the walls from being crushed on each other and therefore from being blocked.

The invention will be more readily understood on reading the following description with reference to the accompanying drawings, in which:

FIG. 1 is a perspective view of an endo-tracheal tube according to the invention.

FIG. 2 is an enlarged front view of a variant embodiment of the thermal shield.

FIG. 3 is a section along line III—III of FIG. 2.

Referring now to the drawings, the endo-tracheal or tracheotomic tube shown in FIG. 1 comprises in known manner a main conduit 1 serving to convey the ventilation and anaesthesia gas from its proximal end 1a up to its distal end 1b and an auxiliary conduit 2 provided with a cannula 2a at its proximal end and incorporated in the conduit 1. The conduit 2 serves to inflate a balloon 3 adapted to ensure tightness with the tissues of the trachea.

Furthermore, the tube 1 comprises, in front of the inflatable balloon 3, a flexible thermal shield 4.

In FIG. 1, this thermal shield 4 is formed by a disc fast with said tube, at right angles to the axis thereof.

On the other hand, in FIGS. 2 and 3, the embodiment of the thermal shield shown is constituted by a plurality of sectors 5 fast at their base with the conduit 1 and partially overlapping one another, like petals. The sectors 5 deform easily when passing through narrow passages, but take back their natural position elastically when the tube is in place in the trachea.

Moreover, the endo-tracheal or tracheotomic tube 1 comprises another auxiliary conduit 6, provided with a cannula 6a at its proximal end and incorporated in the conduit 1 to open out, at its distal end, in an orifice 7 in the wall of the conduit 1. The orifice 7 is located on the side of the shield 4 opposite the balloon 3.

The tube 1 and its different elements 2,3,4 and 6 may be made of different materials: natural elastomers, synthetic polyisoprenes, polychloroprenes, polybutadienestyrenes; polybutadienes, either pure or in combination, may also be suitable. The same applies to plasticized polyvinyl chlorides, polyurethanes . . . , but it is preferable to use polysiloxanes, which are particularly resistant to temperature rise and whose thermal degradation does not involve the formation of caustic or toxic vapours.

In practice, it suffices, to protect the balloon 3 against the laser, that the silicon tube be equipped above the balloon with a shield 4 of diameter slightly smaller than the diameter of the trachea to be intubated and with a thickness of about 6/10 to 8/10 mm, which is for example made of silicone containing aluminium powder.

Experimental tests have shown that a portion of 1% of aluminum by weight guarantees a resistance to 100 pulses of 5/10th second of a laser ray.

Moreover, in order to avoid the tube 1 being crushed when it is bent, a helical coating 8 is advantageously provided, constituted by a strip made of metal or synthetic fibres, for example.

In use, the balloon 3 is inflated and abuts on the walls of the patient's trachea (not shown), inflation being obtained by sending a gas under pressure through conduit 2. Consequently, the balloon 3 ensures separation between the distal end 1b of the conduit 1 and the parts of the tube disposed above the balloon 3. Thus, the oxygen sent in the tube through its end 1a can ventilate the patient's lungs. Similarly, a stream of nitrogen is sent through conduit 6 to leave through orifice 7. The balloon 3 therefore separates two domains where different gaseous atmospheres prevail: below the balloon 3, oxygen leaves through orifice 1b, whilst, above balloon 3, nitrogen leaves through orifice 7.

Laser treatment is therefore carried out in a nitrogen atmosphere. In the event of a communication being made between the domains separated by the balloon 3, the stream of nitrogen leaving through orifice 7 would prevent the oxygen which ventilates the patient's lungs from igniting or from exploding under the action of the laser beam.

What is claimed is:

1. A tracheal device for anesthesia comprising:
    a flexible tubular assembly having a distal end adapted to be positioned within the trachea of a patient and a proximal end positioned outside the body of said patient;
    an inflatable balloon carried on and encircling said tubular assembly adjacent its distal end, said balloon being adapted to be extended by fluid pressure into sealing contact with the trachea;
    a thermal shield adapted to be positioned within the trachea, said shield comprising a flexible generally circular heat-resisting disc substantially coaxial with and transversely affixed to said tubular assembly at a point adjacent said balloon between said balloon and said proximal end, said shield having a diameter only slightly smaller than that of the trachea, thereby effectively shielding said balloon from damage caused by radiant heat energy directed toward said balloon;
    first conduit means in said assembly for conveying anesthesia and ventilation gases from said proximal end to said distal end;
    second conduit means in said assembly for conveying a fluid under pressure from said proximal end to said balloon; and
    third conduit means in said assembly for conveying a stream of inert gas from said proximal end to and through an opening in said assembly at a point adjacent said shield between said shield and said proximal end.

2. The device of claim 1 wherein said tubular body is provided with an external helical strip of a material suitable for maintaining the flexibility of the assembly while protecting said conduits from being crushed as a result of bending of the assembly.

* * * * *